United States Patent [19]

Sundram et al.

[11] Patent Number: 5,843,497
[45] Date of Patent: *Dec. 1, 1998

[54] INCREASING THE HDL LEVEL AND THE HDL/LDL RATIO IN HUMAN SERUM BY BALANCING SATURATED AND POLYUNSATURATED DIETARY FATTY ACIDS

[75] Inventors: Kalyana Sundram, Java, Malaysia; Daniel Perlman, Arlington; Kenneth C. Hayes, Wellesley, both of Mass.

[73] Assignee: Brandeis University, Waltham, Mass.

[ * ] Notice: The term of this patent shall not extend beyond the expiration date of Pat. No. 5,578,334.

[21] Appl. No.: 626,461

[22] Filed: Apr. 2, 1996

Related U.S. Application Data

[63] Continuation-in-part of Ser. No. 418,641, Apr. 7, 1995, Pat. No. 5,578,334.

[51] Int. Cl.[6] .................................................. A23D 9/00
[52] U.S. Cl. .............................. 426/2; 426/601; 426/607; 424/439
[58] Field of Search ................................ 426/607, 2, 601

[56] References Cited

U.S. PATENT DOCUMENTS

| | | | |
|---|---|---|---|
| 3,649,295 | 3/1972 | Bernhart | 426/607 |
| 5,223,285 | 6/1993 | DeMichele | 426/801 |
| 5,380,544 | 1/1995 | Kleman | 426/607 |
| 5,382,442 | 1/1995 | Perlman | 426/804 |
| 5,514,407 | 5/1996 | Perlman | 426/601 |
| 5,578,334 | 11/1996 | Sundram | 426/2 |

OTHER PUBLICATIONS

Agriculture Handbook No. 8–4, U.S.D.A. Science and Education Administration, *Composition of Foods: Fats and Oils*.

Berry et al., "Physicochemical characteristics of palm olein and soybean oil blends," *Palm Oil Technol. Eighties, Rep. Proc. Int. Conf.* pp. 483–498 (1981) (pub. 1983).

Charnock et al., "Dietary modulation of lipid metabolism and mechanical performance of the heart," *3rd Int. Symp. on Lipid Metabolism in the Normal and Ischemic Heart* (Sep. 9–10, 1991).

Choi et al., "Effect of dietary n–3 polyunsaturated fatty acids on cholesterol synthesis and degradation in rats of different ages," *Lipids* 24(1):45–50 (1989).

Demacker et al., "Increased Removal of remnants of triglyceride–rich lipoproteins on a diet rich in polysaturated fatty acids," *European J. of Clin. Invest.* 21:197–203 (1991).

Grundy and Denke, "Dietary Influences on serum lipids and lipoproteins," *J. Lipid Research* 31:1149–1172 (1990).

Grundy, "Comparison of Monounsaturated Fatty Acids and Carbohydrates for Lowering Plasma Cholesterol," *N. Eng. J. Med.* 314:745–748 (1986).

Grundy et al., "Influence of stearic acid on cholesterol metabolism relative to other long–chain fatty acids[1–3]," *American J. Clin. Nutr.* 60(suppl.):986S–990S (1994).

Fujikawa, "Manufacture of Salad Oil," *Jpn. Kokai Tokkyo Koho JP* 61,293,389 [86,293,389] (Dec. 24, 1986).

Haga, "Manufacture of edible Oils," *Jpn. Kokai Tokkyo Koho JP* 61,296,096 [86,296,096] (Dec. 26, 1986).

Han et al., "Effect of palm oil blending on the thermal and oxidative stability of soybean oil," *Han'guk Sikp'um Kwahakhoechi* 23(4):465–70 (1991).

Hayes et al., "Dietary saturated fatty acids (12:0, 14:0, 16:0) differ in their impact on plasma cholesterol and lipoproteins in nonhuman primates[1–4]," *Am. J. Clin. Nutr.* 53:491–498 (1991).

Hayes and Kholsa, "Dietary fatty acid thresholds and cholesterolemia," *FASEB* 6:2600–2607 (1992).

Hegsted et al., "Quantitative Effects on Dietary Fat on Serum Cholesterol in Man," *Amer. J. of Clin. Nutr.* 17:281–295 (1965).

Hegsted et al., "Dietary fat and serum lipids: an evaluation of the experimental data[1–4]," *Amm. J. of Clin. Nutr.* 57:875–883 (1993).

Heyden, "Polyunsaturated and Monosaturated Fatty Acids in the Diet Prevent Coronary Heart Disease via Cholesterol Reduction," *Ann. Nutr. Metab.* 38:117–122 (1994).

Jacobs et al., "Variability in Individual Serum Cholesterol Response to Change in Diet," *Arteriosclerosis*, 3:349–356 (1983).

Kajimoto et al., "Influence of blend ratio of vegetable oils on their thermal oxidation and decomposition of tocopherol," *Nippon Eiyo, Shokuryo Gakkaishi* 44(6):499–505 (1991).

Katan et al., "Effects of fats and fatty acids on blood lipids in humans: an overview1–4," *Am. J. Clin. Nutr.* 60(suppl):107S–1022S (1994).

Khosla and Hayes, "Dietary fat saturation in rhesuss monkeys affects LDL concentrations by modulating the independent production of LDL apolipoprotein B," *Biochem. Biophys. Acta* 1083:46–56 (1991).

(List continued on next page.)

*Primary Examiner*—Carolyn Paden
*Attorney, Agent, or Firm*—Lyon & Lyon LLP

[57] ABSTRACT

A method of increasing the HDL concentration and the HDL/LDL concentration ratio in human serum by providing a balance between a sufficient and required proportion of cholesterol-free saturated fatty acids in the daily dietary fat of the human and a sufficient and required, but not excessive, proportion of polyunsaturated fatty acids comprising linoleic acid in dietary fat, while the remaining proportion of fatty acids and energy from the dietary fat is provided by monounsaturated fatty acids comprising oleic acid. The saturated fatty acids must constitute between 20% and 40% by weight of the daily dietary fat based upon dietary fat accounting for 30% of the total dietary energy consumption, and linoleic acid must constitute between 15% and 40% by weight of dietary fat. In this way, the required proportional intake of polyunsaturated fatty acids enhances the formation of HDL from VLDL and/or decreases the clearance of HDL, while an excessive proportional intake of polyunsaturated fatty acids and monounsaturated fatty acids is avoided to assure a sufficient dietary availability of saturated fatty acids which are required for sufficient VLDL synthesis and HDL production.

16 Claims, 1 Drawing Sheet

OTHER PUBLICATIONS

Khosla and Hayes, "Comparison between the effects of dietary saturated (16:0), monosaturated (18:1), and polyunsaturated (18:2) fatty acids on plasma lipoprotein metabolism in cebus and rhesus monkeys fed cholesterol–free diets," *Am. J. Clin. Nutr.* 55:51–63 (1992).

Kifli et al., "Physical properties of interesterfied palm oil/palm oil fractions with other vegetable oils," *Palm. Oil. Prod. Technol. Eighties, Rep. Proc. Int. Conf.* pp. 303–314 (1981) (published 1983).

Kim, "Relationship between the triacylglycerol composition and foaming of mixed coconut oil under deep–fat frying," *Agric. Biol. Chem.* 52(3):693–699 (1989).

Lim et al., "Oxidative stability of Malaysian palm oil and its blends," *Yukagaku* 39(12):1045–1049 (1990).

Litherland et al., "Preparation of chocolate fats by wet fractionation of soya oil," Abst. of EP 428,200 May 22, 1991, GB 89/25,943 (Nov. 16, 1989).

Majamdar et al., "Vanaspati and margarine fat base from palm oil and palm stearin by corandomization with cottonseed oil," *J. Oil Technol. Assoc. India* 18(2):37–38 (1986).

Mensik and Katan, "Effect of Dietary Fatty Acids on Serum Lipids and Lipoproteins," *Arteriosclerosis and Thrombosis* 12:911–919 (1992).

Murakami et al., "Effect of processed oils and fats on cholesterol metabolism. IV. Effect of palm stearin and changes in its effect by blending with soybean oil and further randomizing," *Yukagaku* 41(3):196–202 (1992).

Murakami et al., "Effect of processed oils and fats on cholesterol metabolism. V. Effect of lard, its blend with palm olein and their randomized oil," *Yukagaku* 41(7):530–537 (1992).

Pronczuk et al., "Dietary myristic, palmitic, and linoleic acids modulate chlesoterolemia in gerbils," *FASEB J.* 8:1191–1200 (1994).

Siguel and Maclure, "Relative Activity of Unsaturated Fatty Acid Metabolic Pathways in Humans," *Metabolism* 36:664–669 (1987).

Sundram et al., "Dietary palmitic acid results in lower serum cholesterol than does a lauric–myristic acid combination in normolipemic humans," *Am. J. Clin. Nutr.* 59:841–846 (1994).

Sundram et al., Fat (Fatty Acid) Modulation of Metabolism (2549–2554) *FASEB J.* 9:A440 (1995) (Abstract).

Suzuki et al., "Fat and oil compositions for frying and spraying," *Jpn. Kokai Tokkyo Koho* JP 01,262,754 [89,262, 754] (Oct. 19, 1989).

Swern, *Baileys Industrial Oil and Fat Products*, vol. 1, 4th edition, John Wiley and Sons, New York pp. 311–332 and pp. 363–368 (1979).

Wai, "A critical review of the cholesterolaemic effects of palm oil," *Food and Nutrition Bulletin* 15:112–123 (1994).

Willet and Sacks, "Chewing the Fat—How Much and What Kind," *N. Eng. J. of Med.* 324:121–123 (1991).

INCREASING THE HDL LEVEL AND THE HDL/LDL RATIO IN HUMAN SERUM BY BALANCING SATURATED AND POLYUNSATURATED DIETARY FATTY ACIDS

BACKGROUND OF THE INVENTION

This application is a continuation-in-part of Sundram et al., U.S. Ser. No. 08/418,641, filed Apr. 7, 1995, now U.S. Pat. No. 5,578,334 entitled "INCREASING THE HDL LEVEL AND THE HDL/LDL RATIO IN HUMAN SERUM WITH FAT BLENDS" hereby incorporated by reference herein.

This invention relates to fats and fat blends, and methods for their manufacture or genetic selection/engineering, and use in foods to stabilize or lower the low density lipoprotein cholesterol (LDL or LDL-C) concentration and increase the high density lipoprotein cholesterol (HDL or HDL-C) concentration in human serum.

Coronary heart disease (CHD) is the major cause of death in the USA and other affluent nations. Plasma cholesterol, more specifically the LDL/HDL ratio, is highly correlated with risk of CHD as documented by Willett and Sacks, 324 N.Eng.J. Med. 121, 1991. The accumulation of LDL in the arterial intima is thought to lead to its oxidation, which in turn results in cascading events that induce arterial occlusion and thrombosis. High concentrations of HDL appear to block LDL oxidation and reduce the atherogenic potential of LDL. Thus, dietary means which decrease the LDL/HDL ratio (or increase the HDL/LDL ratio), especially means which would increase HDL, are desirable. Perlman and Hayes, U.S. Pat. No. 5,382,442 describe modified fat compositions and methods for decreasing total serum cholesterol while simultaneously decreasing the LDL/HDL serum cholesterol ratio. This ratio decreased as both the LDL and HDL concentrations decreased. The net LDL/HDL ratio in the serum decreased only because the LDL cholesterol concentration decreased by a greater factor than serum HDL with the dietary use of a fat-oil blend which included one to ten parts by weight cholesterol-reduced animal fat containing myristic acid, and one part by weight vegetable oil containing linoleic acid.

Within the past three years several authors have collected and analyzed a large number of independent metabolic studies relating to the effect of saturated, monounsaturated, and polyunsaturated fatty acids in the diet on serum LDL and HDL cholesterol levels. These studies have included the techniques of multiple regression analysis to examine LDL and HDL levels versus dietary intake of each group of fatty acids as separate variables expressed as the percentage of dietary energy, i.e., the total daily calorie intake of individuals in the studies.

Mensink and Katan (12 *Arteriosclerosis and Thrombosis* 911, 1992) made the following conclusions; "Replacement of saturated by unsaturated fatty acids raised the HDL to LDL cholesterol ratio, whereas replacement by carbohydrates had no effect. Thus, under isocaloric metabolic-ward conditions the most favorable lipoprotein risk profile for coronary heart disease was achieved if saturated fatty acids were replaced with unsaturated fatty acids, with no decrease in total fat intake." Hegsted et al. (57 *Am. J. Clin. Nutr.* 875, 1993), combined data from 155 human trials in which LDL and HDL cholesterol measurements were available. With regard to fatty acids and cholesterol in the diet, the authors state in their published abstract, "1) saturated fatty acids increase and are the primary determinants of serum cholesterol, 2) polyunsaturated fatty acids actively lower serum cholesterol, 3) monounsaturated fatty acids have no independent effect on serum cholesterol and 4) dietary cholesterol increases serum cholesterol and must be considered when the effects of fatty acids are evaluated. More limited data on low density lipoprotein cholesterol (LDL-C) show that changes in LDL-C roughly parallel the changes in serum cholesterol but that changes in high density lipoprotein cholesterol cannot be satisfactorily predicted from available data." Within this cited article, Hegsted et al. show that LDL levels increase an average of 1.74 mg/dl for each 1% increase in dietary energy represented by saturated fatty acids, while LDL levels decrease an average of 0.77 mg/dl for the corresponding amount of polyunsaturated fatty acids. Referring to the possibility of predicting changes in HDL levels in the serum, these same authors state, "It does not appear possible to develop an equation that predicts changes in HDL-C satisfactorily" and, "The errors in the regression coefficients are large; hence, little reliance should be placed on the equation." These authors calculate a very modest increase in HDL-C correlating with a dietary increase in either saturated or polyunsaturated fatty acids (0.43 mg/dl for a 1 increase in dietary energy represented by saturated fatty acids and 0.22 mg/dl for the corresponding amount of polyunsaturated fatty acids). This indicates that one would expect that for saturated fatty acids, the much smaller increase in HDL (0.43) versus LDL (1.74) per dietary energy, would typically result in a decrease in the HDL/LDL ratio as the saturated fatty acids are increased. On the other hand, the Hegsted et al. and the Mensink and Katan calculations would predict that an increase in the proportion of dietary polyunsaturated fatty acids at the expense of saturated fatty acids would increase the HDL/LDL ratio because this dietary increase caused a large decrease in LDL (approximately 2 mg/dl) and only a small proportional decrease in HDL (approximately 0.2 mg/dl). By comparison, the overall HDL/LDL serum ratios in these studies ranged from approximately 0.25 to 0.50.

Fat blends which include saturated vegetable fats in combination with polyunsaturated vegetable oils have been noted for dietary and/or cooking use. For example, Choi et al., [24(1) Lipids 45, 1989] describe cholesterol synthesis in rats with the feeding of safflower oil or linseed oil blended with palm olein in purified diets containing 10% fat. Suzuki et al., (*Jpn. Kokai Tokkyo Koho* JP 01, 262, 753 [89, 262, 753] 19 Oct 1989), describe the use of 40–90% natural palm oil and 60–5% natural vegetable oil in deep frying. Lim et al., [39(12) Yukagaku 1045, 1990] describe the increased oxidative stability of soybean oil blended with crude or refined palm oil or refined palm kernel oil. Murakami et al., [41 (3) Yukagahu 196, 1992] describe the feeding of soybean oil blended with an equal weight of palm stearin in diets containing 20% fat in which cholesterol metabolism was monitored in rats. Kajimoto et al., [44(6) *Nippon Eiyo, Shokuryo Gakkaishi* 499, 1991] describe the blending of soybean oil or rapeseed oil with palm oil, and the blending of soybean oil, rapeseed oil and palm oil to enhance the oxidative stabilities of the polyunsaturated oils. Han et al., [23 (4) *Han' guk Sikp'um Kwahakhoechi* 465, 1991] describe the stabilization of soybean oil against thermal and oxidative degradation by blending with an equal or greater proportion of palm oil.

SUMMARY OF THE INVENTION

Applicant has determined that in the consumption of dietary fat (as natural triglycerides) it is important to maintain a specific ratio of saturated fatty acids to polyunsaturated fatty acids (at least 0.5:1 but less than 2:1) in the absence of cholesterol. Particularly, it is useful to ingest an adequate proportion of saturated fatty acids contributed by a vegetable oil source such as palm oil, palm olein or its equivalent combined with polyunsaturated fatty acids contributed by a vegetable oil source such as canola oil or soybean oil. Thus, the present invention relates to the dietary use of a cholesterol-free composition in which a balanced proportion of at least one saturated fatty acid such as palmitic acid, myristic acid, and lauric acid is provided together with an approximately equal proportion of at least one polyunsaturated fatty acid such as linoleic acid in the dietary fat. This balanced proportion can be achieved with a mixture of two or more vegetable oils and/or vegetable fats. Alternatively, with recent advances in plant breeding and selection using conventional or genetic engineering methods, the ratio of saturated to polyunsaturated fatty acids provided by single plant species can be manipulated. Thus, in the near future, with suitable plant breeding and selection, a vegetable oil-bearing single plant species may provide, within the range described above, a balanced proportion of saturated and polyunsaturated fatty acids. Furthermore, such plant breeding can provide an enhanced level of alpha-linolenic acid in addition to linoleic acid. There are already a number of examples of successful plant breeding or varietal selection efforts which have led to commercial alternatives in choosing a particular vegetable oil. For example, with the species *Carthamus tinctotius* (safflower), vareties of oil are available with either high oleic acid (>70%) or high linoleic acid (>70%). With the species *Helianthus annuus* (sunflower) varieties of oil are available with either medium (<60%) or high (<60%) levels of linoleic acid. Likewise, canola oil (rapeseed) is available from different varietal sources of two species (*Brassica napus* and *B. campestris*) with erucic acid (22:1) contents from zero to forty percent (see *Baily's Tndustrial Oil and Fat Products,* Vol. 1, D. Swern, ed., Wiley and Sons, New York). Such a composition will increase HDL cholesterol and increase the HDL/LDL ratio (or decrease the LDL/HDL ratio) in the serum of mammals including humans and other primates. According to the present invention, a method is described for increasing the HDL/LDL ratio in human serum in which the HDL concentration increases while the LDL concentration remains essentially constant or decreases. Accordingly, when daily injested fat in the human diet is provided at a level such that it accounts for approximately 30% of the total dietary energy (as currently recommended by the nutritional research community), the saturated fatty acids including palmitic acid, or lauric and myristic acid must constitute between 20% and 40% by weight of the daily dietary fat, and the polyunsaturated fatty acids including linoleic acid must constitute between 15% and 40% by weight of this fat to maximize the serum HDL/LDL ratio. As one example, a cholesterol-free natural triglyceride fat blend containing equal proportions of approximately 30% by weight palmitic acid and 30% by weight linoleic acid plus linolenic acid is useful in the present invention. For this invention to be completely effective, it is important that certain cholesterolemic components be substantially absent from the diet. These components include but are not limited to dietary cholesterol and trans fatty acids, e.g., triglycerides containing elaidic acid produced during partial hydrogenation of vegetable oils. Illustrating this point with a human nutritional study, Sundram et al. (9 FASEB J. 000, 1995, Abstr.) have shown that exchanging trans 18:1 [elaidic acid] for cis 18:1 [oleic acid] caused a large increase in LDL and a decrease in HDL (where trans and cis 18:1 represented respectively, 7% and 16% of the dietary energy). This result and effect is opposite to the desired effect of the present invention.

Applicant has determined that a moderate proportion of saturated fatty acids is beneficial for increasing the HDL/LDL ratio in human serum and that a large proportion of polyunsaturated fatty acids in the dietary fat may, surprisingly, be undesirable in depressing this ratio.

Such advantages are achieved when the diet is essentially free of trans fats (e.g., elaidic) and represents the actual profile of fatty acid intake of the human.

Thus, in a first aspect, the invention features a method of increasing the HDL concentration and the HDL/LDL concentration ratio in human serum. This is achieved by providing a balance between a sufficient and required proportion of cholesterol-free saturated fatty acids in the daily dietary fat of a human, and a sufficient and required, but not excessive proportion of polyunsaturated fatty acids including linoleic acid in dietary fat. The remaining proportion of fatty acids and energy from dietary fat is provided by monounsaturated fatty acids including oleic acid. This means that the saturated fatty acids must constitute between 20% and 40% by weight of the daily dietary fat (based upon dietary fat accounting for 30% of the total dietary energy consumption). It also means that linoleic acid must constitute between 15% and 40% by weight of this dietary fat. These constituents will provide the required proportional intake of polyunsaturated fatty acids and thereby enhance the formation of HDL from VLDL and/or decrease the clearance of HDL. An excessive proportional intake of polyunsaturated fatty acids and monounsaturated fatty acids is also avoided in such a formulation to assure a sufficient dietary availability of saturated fatty acids which are required for sufficient VLDL synthesis and HDL production. Such a dietary fat composition is consistent with the dietary fat composition of the Step I diet of the Mexican Heart Association.

In preferred embodiments, the cholesterol-free saturated fatty acids include palmitic acid, lauric acid and myristic acid; the proportion of monounsaturated fatty acids in the daily dietary fat is between 20% and 50% oleic acid and no greater than 1% elaidic acid (or other unnatural trans fatty acids) by weight; the polyunsaturated fatty acids include linoleic acid and at least one other polyunsaturated fatty acid selected from the group including α-linolenic acid, eicosapentenoic acid (EPA), and docosahexenoic acid (DHA); and the proportion of saturated fatty acids in the daily dietary fat is at least 20% by weight and dietary fat has less than 5% by weight stearic acid.

In a second related aspect, the invention features a method of stabilizing or decreasing the LDL concentration in human serum by providing saturated fatty acids in the daily diet in a proportion between 20% and 40% by weight of the daily dietary fat (based upon dietary fat accounting for 30% of the total dietary energy consumption), and maintaining a proportion of polyunsaturated fatty acids (including linoleic acid) in the daily diet at the expense of monounsaturated fatty acids (including oleic acid and/or elaidic acid). The linoleic acid constitutes between 15% and 40% by weight of dietary fat. Removal of plasma VLDL remnants and LDL is maximized by this formulation, and the production of LDL is reduced.

In a third related aspect, the invention features a method of increasing the HDL and stabilizing or decreasing the LDL concentration in human serum by providing saturated fatty acids in the daily diet in a proportion between 20% and 40% by weight of the daily dietary fat (based upon dietary fat accounting for 30% of the total dietary energy consumption), whereby the production of VLDL, as the HDL precursor, is adequately sustained and is not limiting in HDL biosynthesis. In addition, the method includes maintaining a proportion of polyunsaturated fatty acids (including linoleic acid) in the daily diet at the expense of monounsaturated fatty acids (including oleic acid and/or elaidic acid), wherein linoleic acid constitutes between 15% and 40% by weight of dietary fat, whereby VLDL catabolism to HDL is facilitated and hepatic clearance of VLDL remnants and LDL is enhanced.

In a fourth related aspect, the invention features a method of increasing the HDL concentration and the HDL/LDL concentration ratio in human serum by the dietary consumption of foods prepared using a cholesterol-free single fat composition or blended fat composition containing a ratio of one part by weight polyunsaturated fatty acids to at least one part by weight saturated fatty acids. The single fat composition or blended fat composition includes linoleic acid and at least one saturated fatty acid selected from the group including lauric acid, myristic acid, and palmitic acid. The linoleic acid constitutes between 15% by weight and 40% by weight of the composition and saturated fatty acid constitutes between 20% and 40% by weight of the composition. In this way, adequate dietary levels of saturated fatty acids in the absence of cholesterol stimulate VLDL synthesis and secretion by the liver, and adequate dietary levels of linoleic acid enhance LPL activity and generation of HDL from VLDL while stimulating the removal of VLDL remnants and LDL, and concomitently decreasing CETP activity and HDL catabolism.

In preferred embodiments of the above aspects, the food-source of saturated fatty acids includes at least one vegetable fat selected from the group including palm fat, coconut fat and cocoa butter; the palm fat is selected from the group including palm oil, palm olein, and palm kernel oil; the food source of polyunsaturated fatty acids includes at least one vegetable oil selected from the group including corn oil, sunflower oil, safflower oil, soybean oil, cottonseed oil, canola oil, and peanut oil; alternatively, the food source of both saturated fatty acids and polyunsaturated fatty acids is a single vegetable oil species which has been selected or engineered to provide the requisite balance of saturated and polyunsaturated fatty acids; the polyunsaturated fatty acids include linoleic acid and linolenic acid; wherein linolenic acid is contributed by soybean oil, canola oil, edible flax seed oil, and/or perrilla seed oil; within the single fat composition or blended fat composition is provided a proportion of at least one part by weight cholesterol-free saturated fat to one part by weight polyunsaturated fat to stabilize the polyunsaturated fat against oxidation; the oxidation-resistance of the single fat or blended fat composition upon heating to a temperature of 100° C. or greater in air is increased by at least 25% compared to the oxidation resistance of the polyunsaturated fat component when heated separately from the single fat or blended fat composition; essentially all of dietary fat is provided in a nutritionally balanced liquid and/or solid formula diet in which dietary fat accounts for between 15% and 45% of the total dietary energy consumption; the dietary fat accounts for between 20% and 30% of the total dietary energy consumption; the compositions noted above are used in place of dietary consumption of foods prepared using a blended fat composition, that is, such foods are substituted with the dietary consumption of a nutritionally balanced liquid formula diet prepared using a single fat or blended fat composition in which the total fat content therein accounts for between 15% and 45% of the total dietary energy consumption; daily dietary fat or foods contain a blended fat composition including one part by weight of at least one polyunsaturated vegetable oil selected from the group including corn oil, sunflower oil, safflower oil, soybean oil, cottonseed oil, canola oil, and peanut oil blended with at least one part by weight of vegetable fat including saturated fatty acids; the vegetable fat is selected from the group including palm fat, coconut fat and cocoa butter; and the palm fat is selected from the group including palm oil, palm olein, and palm kernel oil. Alternatively the daily dietary fat or foods contain a single vegetable oil species which has been selected or engineered to provide the requisite balance of saturated and polyunsaturated fatty acids.

In a fourth related aspect, the invention features a method of increasing the HDL concentration and the HDL/LDL concentration ratio in human serum by the dietary consumption of foods. These foods are prepared using at least one modified fat selected from the group including a chemically interesterified fat, an enzymatically interesterified fat, and a synthetic fat. The modified fat includes one part by weight polyunsaturated fatty acids and at least one part by weight saturated fatty acids selected from the group including lauric acid, myristic acid, and palmitic acid. The polyunsaturated fatty acids constitute between 15% by weight and 40% by weight of modified fat, and the saturated fatty acids constitute between 20% and 40% by weight of modified fat. In this way adequate dietary levels of saturated fatty acids in the absence of cholesterol stimulate VLDL synthesis and secretion by the liver, and adequate dietary levels of polyunsaturated fatty acids enhance LPL activity and generation of HDL from VLDL while stimulating the removal of VLDL remnants and LDL and concommitently decreasing CETP activity and HDL catabolism (FIG. 1).

Preferably, the weight ratio of saturated fatty acids to polyunsaturated fatty acids included in dietary fat, modified fat, or blended fat composition ranges from 0.5: 1.0 to 2.0:1.0; and the weight ratio is approximately (+20%) 1 to 1.

In a fifth related aspect, the invention features a liquid and/or solid dietary composition suitable for human or animal ingestion for increasing the HDL concentration and the HDL/LDL concentration ratio in the blood serum. Essentially all of dietary fat which accounts for between 15% and 45% of the total dietary energy in liquid formula diet, is provided by a single fat or a blended fat composition containing one part by weight polyunsaturated fat and at least one part by weight cholesterol-free saturated fat. The single fat or blended fat composition includes linoleic acid and at least one saturated fatty acid selected from the group including lauric acid, myristic acid, and palmitic acid. The linoleic acid constitutes between 15% by weight and 40% by weight of the composition, and saturated fatty acid constitutes between 20% and 40% by weight of composition.

In preferred embodiments, dietary fat accounts for between 20% and 30% of the total dietary energy in the liquid formula diet; the saturated fatty acid is predominantly palmitic acid; and a reduction in cardiac arrythmia accompanies the increase in HDL concentration and the increase in HDL/LDL concentration ratio.

Suitable sources for cholesterol-free fats containing saturated fatty acids include saturated vegetable fats such as palm fat, coconut fat, and cocoa butter. Palm oil, palm olein, and palm kernel oil are particularly useful sources for the saturated fatty acids. Suitable sources for polyunsaturated fatty acids include the vegetable oils which are rich in linoleic acid such as corn oil, sunflower oil, safflower oil, soybean oil, and cottonseed oil for example. The above-mentioned vegetable fats and oils can be blended in appropriate ratios according to the content of the above-mentioned saturated and polyunsaturated fatty acids therein, to produce dietary fat blends having the recommended proportions by weight of saturated and polyunsaturated fatty acids (see Tables I and II for the fatty acid content of various vegetable fats and oils as derived from published data [Agriculture Handbook No. 8–4, U.S.D.A. Science and Education Administration, *Composition of Foods: Fats and Oils*]).

balanced mixture of saturated and polyunsaturated fatty acids can be provided not only as a natural blend of cholesterol-free saturated fats and polyunsaturated oils, but also as a mixed fatty acid composition in the form of one or more modified or synthetic fats incorporating chemically or

TABLE I

POLYUNSATURATED VEGETABLE OILS

|  | Safflower | Sunflower | Corn | Cottonseed | Soybean | Peanut | Canola |
|---|---|---|---|---|---|---|---|
| SATs (wt %) | | | | | | | |
| total | 9.1 | 10.3 | 12.7 | 25.9 | 14.4 | 16.9 | 7.1 |
| 14:0 | 0.1 | | | 0.8 | 0.1 | 0.1 | |
| 16:0 | 6.2 | 5.9 | 10.9 | 22.7 | 10.3 | 9.5 | 4.0 |
| 18:0 | 2.2 | 4.5 | 1.8 | 2.3 | 3.8 | 2.2 | 1.8 |
| MONOs (wt %) | | | | | | | |
| total | 12.1 | 19.5 | 24.2 | 17.8 | 23.3 | 46.2 | 58.9 |
| 18:1 | 11.7 | 19.5 | 24.2 | 17.0 | 22.8 | 44.8 | 56.1 |
| 20:1 | | | | | 0.2 | 1.3 | 1.7 |
| POLYs (wt %) | | | | | | | |
| total | 74.5 | 65.7 | 58.7 | 51.9 | 57.9 | 32.0 | 29.6 |
| 18:2 | 74.1 | 65.7 | 58.0 | 51.5 | 51.0 | 32.0 | 20.3 |
| 18:3 | 0.4 | | 0.7 | 0.2 | 6.8 | | 9.3 |

TABLE II

SATURATED VEGETABLE FATS

|  | Coconut Oil | Cocoa Butter | Palm Oil | Palm Olein | Palm Kernel Oil |
|---|---|---|---|---|---|
| SATs (wt %) | | | | | |
| total | 86.5 | 59.7 | 49.3 | 43.7 | 81.4 |
| 12:0 | 44.6 | | | | 47.0 |
| 14:0 | 16.8 | 0.1 | 1.0 | 0.8 | 16.4 |
| 16:0 | 8.2 | 25.4 | 43.5 | 38.9 | 8.1 |
| 18:0 | 2.8 | 33.2 | 4.3 | 4.0 | 2.8 |
| MONOs (wt %) | | | | | |
| total | 5.8 | 32.9 | 37.0 | 45.0 | 11.4 |
| 18:1 | 5.8 | 32.6 | 36.6 | 45.0 | 11.4 |
| 20:1 | | | 0.1 | | |
| POLYs (wt %) | | | | | |
| total | 1.8 | 3.0 | 9.3 | 11.3 | 1.6 |
| 18:2 | 1.8 | 2.8 | 9.1 | 10.9 | 1.6 |
| 18:3 | | 0.1 | 0.2 | 0.4 | |

For example, two parts palm oil (44% palmitic acid, 9% linoleic acid) can be blended with one part corn oil (11% palmitic acid, 58% linoleic acid) to provide a balanced fat blend containing approximately 33% palmitic acid (16:0) and 25% linoleic acid (18:2). Such cholesterol-free balanced fat blends are useful not only as dietary constituents that modulate plasma cholesterol to maximize the HDL/LDL ratio but also provide advantageous use in various cooking procedures such as in deep-fat frying. The fat blends may also be used in shortening for baked prepared foods (including cakes, pies, cookies, crackers, etc.), in dairy products (including frozen desserts, creams, cheeses, spreads), and in blended food products (including salad dressing, margarines, mayonnaise). In addition the fat blends may be used in liquid and/or solid dietary compositions for managing and controlling food intake such as for weight loss, control of hypercholesterolemia, or for managing any one of a variety of health conditions requiring a controlled diet in which the proportion and composition of the dietary fat must be controlled. As a practical matter, the enzymatically interesterified fatty acids to achieve the balanced proportion of saturated and polyunsaturated fatty acids described in this invention.

Other features and advantages of the invention will be apparent from the following description of the preferred embodiments thereof, and from the claims.

DESCRIPTION OF THE PREFERRED EMBODIMENTS

The drawing will first briefly be described.

DRAWING

The Figure is a diagrammatic representation of lipoprotein metabolism.

FATTY ACID BALANCE

To understand the significance of, and reason for balancing the proportion of saturated and polyunsaturated fatty acids by selecting or engineering a single vegetable oil species, or by blending two or more vegetable oils and/or fats for including in the fat-containing foods mentioned above such as cooking fats, prepared baked foods, dietary foods, and the like, one must understand some of the important parameters governing lipoprotein and cholesterol synthesis and catabolism (see Figure).

The LDL/HDL ratio, and changes in this ratio depend upon a number of metabolic variables such as hormonal, metabolic, environmental and nutritional perturbations including changing dietary fat compositions which affect lipoprotein levels. As detailed in FIG. 1, it can be seen that both LDL and HDL are derived, in part, by the catabolic events resulting in the breakdown of VLDL (very low density lipoprotein), the TG (triglyceride)-rich lipoprotein secreted by the liver for the purpose of delivering TG to muscle for energy generation or to adipose tissue for storage. In humans, the breakdown of VLDL is a major source of HDL as well as the primary origin of LDL as described by Grundy et al., 31 *J. Lipid Res.* 1149, 1990. Thus, the potential mass for both HDL and LDL generation is dependent, in part, upon the production rate (mass per unit time) of VLDL secreted by the liver. On the other hand, reduction in the final pool of circulating LDL depends both upon the proportion of the VLDL remnants which are retained and cleared by the liver directly (reducing diversion to LDL) as well as the rate of LDL removal by the liver once LDL is formed. Both VLDL remnants and LDL are cleared via liver receptors ($LDL_r$), and both represent a "sink" for receiving HDL cholesterol esters (CE) via CETP (cholesterol ester transfer protein, see below), thereby reducing the HDL pool once it has been formed. The main function of HDL in this cholesterol-shuttle pathway is to "clean-up" the cholesterol excess "spilled" during VLDL catabolism and then deliver it (as indicated above) as CE either to VLDL remnants or to LDL. These lipoproteins can then carry cholesterol back to the liver for excretion as bile acids (or biliary free cholesterol). Both the catabolism of VLDL involving release of TG, and the CE shuttle from HDL to VLDL-LDL are controlled by proteins that are affected by dietary fat. The former process is modulated by lipoprotein lipase (LPL) and the latter by the transfer protein CETP. These proteins are affected oppositely by the presence of saturated (SAT) and trans (elaidic acid-containing) fats on the one hand, versus polyunsaturated (POLY) fat on the other hand. SAT and trans fats induce increased CETP activity which is associated with increased LDL, and trans fats can even decrease HDL. However POLYs reduce the activity of CETP and enhance LPL activity and favor formation of HDL from VLDL as shown by Demacker et al., 21 *Eur. J. of Clin. Invest.* 197, 1991.

Applicant and other investigators have found that dietary fatty acids consumed in the form of natural fats or fat blends affect different lipoproteins and their concentrations in a number of ways. For example, for more than 30 years it has been appreciated that saturated fat increases total cholesterol (TC), whereas polyunsaturates decrease it, and monounsaturates were thought to be neutral (see Hegsted et al., 17 *Am.J. of Clin. Nutr.* 281, 1965, Hegsted et al., 57 *Am. J. of Clin. Nutr.* 875, 1993, and Heyden, 38 *Ann. Nutr. Metab.* 117, 1994). More recently, investigators have focused on nutritional variables by which the different species of lipoproteins, as opposed to TC, are affected. The consensus is that most saturated fatty acids consumed as fats, i.e., twelve to fourteen carbon saturated fatty acids including lauric, myristic, and palmitic acids (12:0, 14:0, and 16:0 respectively), have the potential for elevating both LDL and HDL, although the relative increase in LDL tends to be greater than that for HDL (see Grundy et al., 31 *J. Lipid Res.* 1149, 1990, Pronczuk et al., 8 *FASEB J.*, 1191, 1994, Katan et al., 60 suppl. *Am. J. Clin. Nutr.* 1017S, 1994 and Mensink et al., 12 *Arteriosclerosis and Thrombosis* 911, 1992). Adding to the complexity, 14:0-rich TGs are more cholesterolemic than 16:0-rich TGs (see Hegsted et al., 17 *Am. J. Clin. Nutr.* 281, 1965, Sundram et al., 59 *Am. J. Clin. Nutr.* 841 1994, Hayes et al., 53 *Am. J. Clin. Nutr. 491, 1991,* and Hayes et al., 6 *FASEB J.* 2600, 1992), and the impact of 16:0 is highly dependent on the host "metabolic setpoint" for TC in the serum at the time of intervention. Thus in people with high TC, 16:0 acts as a cholesterol-raising fatty acid, but at TC<200 mg/dl 16:0 typically appears neutral, neither raising nor lowering TC (see Heyden, 38 *Ann. Nutr. Metab.* 117, 1994, and Hayes et al., 53 *Am. J. Clin. Nutr.* 491, 1991). On the other hand, 14:0-rich TGs are always cholesterol-raising, suggesting a different regulatory role for 14:0 and 16:0. Natural TGs, i.e. fats containing the 12:0 fatty acid also contain 14:0, so for all practical purposes they can be considered together (12:0 +14:0) and separate from 16:0, which is generally the most prevalent saturated fatty acid in fats derived from plant and animal sources, often without any 12:0+14:0. Surprisingly, stearic acid (18:0) seems to be neutral in its regulatory behavior over TC (see Hegsted et al., 57 *Am. J. Clin. Nutr.* 875, 1993 and Katan et al., 60 suppl. *Am. J. Clin. Nutr.* 1017S, 1994)

Only one fatty acid, linoleic acid (18:2n6 or 18:2), is generally acknowledged to be cholesterol-lowering. As an essential or required dietary polyunsaturated fatty acid, it alone among all of the POLYs [including linolenic or 18:3n3, eicosapentenoic (EPA) or 20:5n3, and docosahexenoic acid (DHA) or 22:6n3] consistently lowers TC, especially lowering LDL-C but also decreasing HDL-C at high dietary intake of POLYs (Grundy et al., 31 *J. Lipid Res.* 1149, 1990, Hegsted et al., 17 *Am. J. Clin. Nutr.* 281, 1965, and Hegsted et al., 57 *Am. J. Clin. Nutr.* 875, 1993). In fact, this tendency for 18:2 to lower HDL has even led to warnings against recommending POLYs as a means for lowering TC. Rather, the recommendation has been offered that monounsaturated fats (MONOs) containing oleic acid (18:1) should replace saturated fat as much as possible because MONOs do not lower HDL like POLYs do, and replacing saturates with MONOs will primarily lower LDL as suggested by Grundy et al., 31 *J. Lipid Res.* 1149, 1990.

As applicant will describe below, the later statement is true, but it ignores the critical role of POLYs, and the fact that it is a critical balance between dietary intake of SATs and POLYs (both at moderate intake) which actually allows HDL to increase to yield the highest serum HDL/LDL ratio, at least in humans with normal cholesterol metabolism.

Over the past few years a number of nutritional experiments using animal models and humans are relevant to Applicant's finding of fatty acid proportions required for generating the highest HDL/LDL ratio. The first relevant study was in monkeys (Hayes et al., 53 *Am. J. Clin. Nutr.* 491, 1991). In that report it was found that for SATs, 16:0 increased TC less than 12:0+14:0, but quite surprisingly 16:0 had an effect on TC very similar to POLYs (18:2) when 5% of the daily dietary calorie intake (abbreviated 5% en) was exchanged between these 2 fatty acids (between 5–10% en as 18:2, i.e. Diets 4 vs. 5 in the cited study). At the time of the study, the authors failed to appreciate the significance of the fact that once 5% en as 18:2 in the daily diet has been achieved, additional dietary 18:2 does not really exert much effect on TC and can be exchanged for other "neutral" fatty acids without altering TC appreciably. This relationship has been described as the "threshold effect" for 18:2 (Hayes et al., 6 FASEB J. 2600, 1992 and Pronczuk et al., 8 FASEB J. 1191, 1994).

In a second study in rhesus monkeys (Khosla et al., 1083 Biochem. et Biophys. Acta 46, 1991), the authors explored possible metabolic reasons for differences observed in TC during the exchange of (16:0+18:1) for (12:0+14:0) [Diet 4 versus Diet 2 in the cited study]. It was found that the former fatty acids (16:0+18:1) led to 3-fold more VLDL output than the (12:0+14:0) diet, and that the (12:0+14:0) diet produced a larger LDL pool and a poorer (lower) HDL/LDL ratio. The authors interpreted this to mean that dietary (12:0+14:0) fatty acids were worse than 16:0 (and 18:1) in terms of raising LDL, presumably because (12:0+14:0) down-regulate the $LDL_r$ making it difficult for VLDL remnants and LDL particles to be cleared by the liver. This ultimately causes LDL to accumulate.

In a third monkey study (Khosla et al., 55 Am.J. Clin. Nutr. 51, 1992) the effect of high dietary intake of SAT 16:0 in the form of palm oil, versus high dietary intake of MONO 18:1 in the form of high oleic safflower oil, and also versus high dietary intake of POLY 18:2 in the form of high linoleic safflower oil was examined. Here the TC response was animal species specific, with all three fats causing an equal TC response in rhesus. However the high dietary 18:2 (at 30% en) produced lower TC in the cebus species by virtue of an undesirable depressed HDL-C level while the LDL-C was unaffected by all three diets in both species. These data indicated that genetic differences can affect the sensitivity to 18:2 in the diet, but that 16:0, 18:1, and 18:2 can appear to exert similar effects when lipoprotein metabolism is unimpaired and when essentially no dietary cholesterol is present to interfere with LP metabolism (especially by decreasing LDL receptor number and LDL clearance rate).

An interesting observation and measurement recorded in the above cited study and unexplained until now was a favorable HDL/LDL ratio which was greater in monkeys fed the 16:0-containing SAT diet than the MONO or POLY diet. This observation contradicted the generally held belief that dietary SATs should be avoided in favor of POLYs and MONOs. However, this early measurement taken together with the more extensive new data provided in Appendix I now indicate that saturated fatty acids are a necessary dietary component for increasing HDL and increasing the HDL/LDL ratio in the serum.

In other previous experiments using saturated animal fats blended with POLYs described in Perlman and Hayes, supra, it is noted that rodents (gerbils and hamsters) and monkeys (cebus) exhibited unexpectedly increased HDL/LDL lipoprotein ratios when corn oil (rich in 18:2) was blended into animal fats stripped of cholesterol. These data are also consistent with the model now proposed in which a balanced ratio of SATs and POLYs in the diet may be the most important consideration in modulating lipoproteins to increase HDL and maximize the HDL/LDL ratio.

The discovery confirming and validating applicant's new model appears in the human nutritional study involving three different diets described in Sundram et al. (hereby incorporated by reference in totality, Nutrional Biochemistry Vol 6:179–187, 1995). The most critical results from this study are summarized in Table III.

TABLE III

HDL CONCENTRATION IN HUMAN SERUM VARIES WITH RATIO OF SATURATED TO POLYUNSATURATED FATTY ACIDS IN DIETARY FAT

| Dietary Fat (code) | Dietary Fat Composition (Weight Percentage) | | | Percent Dietary Energy (Percentage of Daily Calories) | | | Serum Cholesterol (mg/dl concentration) | | |
|---|---|---|---|---|---|---|---|---|---|
| | SAT | MONO | POLY | 16:0 SAT | 18:1 MONO | 18:2 POLY | HDL-C | LDL-C | TC |
| CAN | 7 | 57 | 36 | 4 | 17 | 6 | 49 | 97 | 177 |
| POL | 44 | 45 | 11 | 11 | 13 | 3.5 | 49 | 102 | 181 |
| AHA | 30 | 37 | 33 | 8 | 12 | 7 | 57 | 96 | 179 |

These diets included one containing low dietary SATs combined with moderate POLYs and high MONOs (canola oil diet-abbreviated CAN), a second containing high dietary SATs combined with low POLYs and moderate MONOs (palm olein-abbreviated POL), and a third containing moderate dietary SATs combined with moderate POLYs and moderate MONOs (soybean oil-palm olein-canola oil blend-abbreviated AHA). Indeed, all three fat-containing diets produced equal TC and similar LDL-C, but the AHA fat blend increased HDL-C by 20% (see Table III) relative to the other two diets. Thus, Applicant unexpectedly discovered that normolipemic people (i.e., people with normal lipoprotein metabolism and exhibiting serum TC values of <200 mg/dl) appear to require moderate levels of both SATs and POLYs which, in appropriate total dietary amounts, produce an increased HDL concentration and increased HDL/LDL ratio in the serum.

In order to provide a general method for maximizing the HDL/LDL ratio in human serum it is useful to understand the physiological basis by which the HDL/LDL ratio may be altered. Returning to FIG. 1 and the experimental observations reported on herein, it appears that SATS (16:0 in the above diet) drive VLDL output, maximizing the potential for HDL production (i.e., increasing the HDL precursor pool of VLDL). Since high dietary levels of MONOs did not increase HDL while moderate levels of SATs did increase HDL, it would appear that 16:0 (not 18:1) may have been responsible for the greatest VLDL output in the previous rhesus study (Khosla et al., 55 Am. J. Clin. Nutr. 51, 1992). Secondly, it seems that an adequate intake of POLYs [which must exceed the 3.3% en shown to be sub-optimal in the low-POLY diet in the appendix is needed to assure up-regulated or stimulated $LDL_r$ activity. This level of POLYs is estimated to be at least 5–6% en and has been described elsewhere as "assuring the 18:2 threshold requirement" (Hayes et al., 6 FASEB J. 2600, 1992 and Pronczuk et al., 8 FASEB J. 1191, 1994). This intake of POLYs also assures that VLDL catabolism and LDL clearance proceeds efficiently and rapidly (decreasing plasma LDL) while sparing the need for HDL "clean-up" (ultimately increasing available HDL). Viewed as a balancing process, adequate SATs are needed to enhance HDL precursor output (as VLDL) and adequate POLYs are needed to keep LDLr up-regulated to enhance LDL and VLDL remnant clearance by the liver. Together this combination results in the highest HDL and lowest LDL levels in the serum. To applicant's knowledge neither this combination of fatty acids nor this rationale for metabolic function has ever been recognized, let alone demonstrated in humans prior to this time.

The importance of diversifying the dietary intake of polyunsaturated fatty acids to include one or more of the omega3 polyunsaturates [i.e., α-linolenic acid (18:3, omega3), eicosapentenoic acid (EPA) and docosahexenoic acid (DHA)], in addition to linoleic acid (18:2, w6), has recently been pointed out by Charnock et al. ($3^{rd}$ Int. Symp. on Lipid Metabolism in the Normal and Ischemic Heart, Sept. 1991) and by McLennan et al. (19 Aust. NZ J. Med. 1, 1989). According to these investigators, adding the above-mentioned omega3 polyunsaturated fatty acids to the diet improved the mechanical performance and the electrical stability of the marmoset heart. In this animal model the incidence of ventricular fibrillation was reduced while ventricular ejection, peak filling rate and end diastolic volume increased when compared to animals fed similar diets containing only polyunsaturates of the w6 type, e.g., linoleic acid. In marmosets fed saturated animal fats in place of comparable amounts of sunflower oil (linoleic acid-rich oil) or fish oil (omega3-rich oil), cardiac performance deteriorated significantly with respect to both mechanical and electrical parameters.

As taught in the present invention, there are several straightforward means of providing a mix, and controlling the balance of saturated and polyunsaturated fatty acids in ones daily dietary fat. In the extreme case, the strictly controlled use of liquid and/or solid dietary formulations which provide all of the dietary fat can be used to insure this balance. In a moderately controlled setting, institutional preparation of food for resident populations allows the monitored use of fats, e.g., hospital, university, and military kitchens, in which appropriately balanced fat blends can be used throughout the food preparation scheme. In addition, manufacturers of prepared food such as commercial bakers can use appropriately balanced blends of fats and oils.

Example 1: Fat Blends for Increasing the HDL Concentration and the HDL/LDL Ratio Two parts palm oil (44% palmitic acid, 9% linoleic acid) are blended with one part corn oil (11% palmitic acid, 58% linoleic acid) to provide a balanced fat blend containing approximately 33% palmitic acid (16:0) and 25% linoleic acid (18:2). When consumed as the principal and essentially the sole source of dietary fat in the daily diet, and representing approximately 30% of the dietary energy this fat blend will increase the level of HDL cholesterol in human serum and the HDL/LDL ratio compared to a similar diet in which the proportion of either palmitic acid or linoleic acid is 3-fold lower.

Example 2: Other Fat Blends for Increasing HDL and the HDL/LDL Ratio

One part palm oil (44% palmitic acid, 9% linoleic acid) is blended with one part cottonseed oil (23% palmitic acid, 52% linoleic acid) to provide a fat blend containing approximately 34% palmitic acid and 31% linoleic acid. One part palm oil is blended%with one part soybean oil (10% palmitic acid, 51% linoleic acid and 7% linolenic acid) to provide a fat blend containing approximately 27% palmitic acid, 30% linoleic acid and 3% linolenic acid. Alternatively, one part coconut oil (approximately 70% lauric, myristic, and palmitic acids, and 2% linoleic acid) is blended with one part sunflower oil (6% palmitic acid, 66% linoleic acid) to provide a different balanced fat blend containing approximately 38% C12–C16 mixed saturated fatty acids and 34% linoleic acid. Alternatively, in a three component system, one part palm kernel oil (47% lauric acid, 16% myristic acid, 8% palmitic acid, and 2% linoleic acid) is blended with one part corn oil (11% palmitic acid and 58% linoleic acid) and one part canola oil (4% palmitic, 20% linoleic acid and 9% linolenic acid) to provide a fat blend containing 29% C12–C16 mixed saturated fatty acids, 27% linoleic acid, and 3% linolenic acid. In another three component system termed the AHA blend (see Table I), four parts palm oil are blended with five parts soybean oil and one part canola oil to provide a fat blend containing 26% palmitic acid, 29% linoleic acid, and 3% linolenic acid. In still another three component system, three parts palm olein (39% palmitic acid, 11% linoleic acid) are blended with one part cottonseed oil (23% palmitic acid, 52% linoleic acid) and one part safflower oil (6% palmitic acid, 74% linoleic acid) to provide a fat blend containing 29% palmitic acid and 32% linoleic acid.

Example 3: Oxidation-Resistant Fat Blends for Food Preparation as well as for Increasing the HDL Concentration and the HDL/LDL Ratio Consistent with Examples 1 and 2, blends useful for increasing the HDL level and the HDL/LDL ratio in human serum include four to nine parts palm olein (39% palmitic acid, 11% linoleic acid) blended with one part of corn oil (11% palmitic acid, 58% linoleic acid) to provide a dietary fat blend containing approximately 33% to 36% palmitic acid and 20% to 16% linoleic acid. Similarly, two parts palm olein are blended with one part of corn oil to provide a fat blend containing approximately 30% palmitic acid and 27% linoleic acid. Likewise, as illustrated in Example 1, two parts palm oil are blended with one part corn oil for use as a dietary fat. These and other blends of vegetable fats and oils have been found to be valuable as ingredients in baked, fried, and other prepared foods, e.g., salad dressings, desserts, etc. because of the increased oxidative stabilities of these blends in combination with their metabolic benefits already described. The increase in oxidative stability for the polyunsaturated vegetable oil component in these blends is reflected in a longer shelf life for foods prepared using these blends, and a longer cooking (i.e., frying) lifetime for these blends when they are maintained at an elevated temperature (approximately 350° F.) for many hours.

By way of specific example, when blended with palm oil or palm olein, the oxidation-resistance of certain polyunsaturated vegetable oils is increased relative to that of the same oil when heated separately from the blended composition. In this Example and in Table IV, the stability of various oils and blends was measured by the Rancimat method in which the oxidative stability is directly proportional to the Rancimat number provided. A fat blend in which the oxidative stability of the blend is at least 25% greater than that of the polyunsaturated vegetable oil component in the blend is considered an oxidation-resistant blend for the purposes of this invention.

The extent of oxidation-resistance in such blends has been found to vary widely depending upon the type of vegetable oil (e.g., corn versus soybean oil) and the extent of its dilution into the saturated fat such as palm fat. Accordingly, it is apparent from Table IV that at higher dilutions of polyunsaturated vegetable oils (e.g., 5-fold and 10-fold dilutions of soybean oil into the palm fats), the fat blends maintains good stability. However, when diluted only 3.3-fold (see 2.3:1 column in Table IV), and within the composition range nutritionally useful in the present invention, the oxidative stability of the soybean oil-palm fat blends can fall to approximately the same level as the unblended vegetable oil (cf. 7.6 and 5.6 for the blends versus 6.3 for the soybean oil alone). Surprisingly however, Table IV reveals that corn oil can be stabilized against oxidation at both lower (3.3-fold) and higher (5 and 10-fold) dilutions with palm fat. Thus, the oxidative stability of the corn oil-palm blends is at least two-fold greater than the corn oil alone (cf. 11.2 and 9.9 for the lower dilution blends versus 4.8 for the corn oil alone). The results from this Table and from previous unpublished experiments of Applicant have shown that the oxidative stability of fat and oil blends is unpredictable and can only be determined by experimentation. It is significant that the proportions of a number of fats and oils in such blends which are useful in the diet for controlling cholesterol levels as taught herein, are also useful owing to their oxidative stabilities.

TABLE IV

OXIDATIVE STABILITY OF FAT
(Rancimat method*)

| Ratio | (Palm olein:Polyunsaturated oil) | | |
|---|---|---|---|
| Polyunsaturated oil | 9:1 | 4:1 | 2.3:1 |
| soybean | 16 | 14.4 | 7.6 |
| corn | 16.7 | 13.5 | 11.2 |

| Ratio | (Palm oil:Polyunsaturated oil) | | |
|---|---|---|---|
| Polyunsaturated oil | 9:1 | 4:1 | 2.3:1 |
| soybean | 14.4 | 10.2 | 5.6 |
| corn | 15.3 | 12.2 | 9.9 |

OXIDATIVE STABILITY OF PURE FATS AND OILS

| Palm olein | 20 |
|---|---|
| Palm oil | 21.2 |
| soybean oil | 6.3 |
| corn oil | 4.8 |

*The Rancimat method determines the oxidative and thermal stability towards oxidative decomposition in oils and fats. The oil sample is exposed to a stream of atmospheric oxygen at elevated temperatures giving rise to organic acids in the oil/fat. These volatile products are trapped in a measuring vessel filled with distilled water and continuously detected with a conductivity cell. The measurements are then evaluated by a control unit which records the induction time of the sample. The progress of the oxidation curve determined in this manner virtually parallels the development of the peroxide values in the oils being tested.

Other embodiments are within the following claims.

We claim:

1. A cholesterol-free fat composition suitable for human or animal ingestion for increasing the HDL concentration and the HDL/LDL concentration ratio in the blood serum, wherein said fat composition contains one part by weight polyunsaturated fat and at least one part by weight cholesterol-free saturated fat, where said fat composition comprises linoleic acid and at least one saturated fatty acid selected from the group consisting of lauric acid, myristic acid, and palmitic acid, said linoleic acid constituting between 15% by weight and 40% by weight of the fat in said fat composition and said saturated fatty acid constituting between 20% and 40% by weight of the fat in said fat composition, and wherein said fat composition comprises no more than 1% elaidic acid or other unnatural trans fatty acids by weight.

2. The fat composition of claim 1, wherein said fat composition is a component of a controlled diet, wherein the proportion and composition of the dietary fat in said diet are controlled.

3. The composition of claim 1, wherein said composition is suitable for deep fat frying.

4. The composition of claim 1, wherein said composition is suitable for use in a food product selected from the group consisting of baked prepared foods, dairy products, and blended food products.

5. The composition of claim 4, wherein said baked prepared foods, dairy products, and blended food products are selected from the group consisting of pies, cookies, crackers, frozen desserts, creams, cheeses, spreads, salad dressing, margarines, and mayonnaise.

6. The composition of claim 1, wherein the balanced mixture of saturated and polyunsaturated fatty acids is provided by fats selected from the group consisting of a single fat, a natural blend of cholesterol-free saturated fats and polyunsaturated oils, and modified or synthetic fats incorporating chemically or enzymatically interesterified fatty acids.

7. A prepared food product, comprising a cholesterol-free fat composition suitable for human or animal ingestion for increasing the HDL concentration and the HDL/LDL concentration ratio in the blood serum, comprising one part by weight polyunsaturated fat and at least one part by weight cholesterol-free saturated fat, where said fat composition comprises linoleic acid and at least one saturated fatty acid selected from the group including lauric acid, myristic acid, and palmitic acid, said linoleic acid constituting between 15% by weight and 40% by weight of the fat in said fat composition and said saturated fatty acid constituting between 20% and 40% by weight of the fat in said fat composition.

8. The prepared food product of claim 7, wherein the fat in said prepared food product consists essentially of said cholesterol-free fat composition.

9. The prepared food product of claim 7, wherein said prepared food product is selected from the group consisting of baked prepared foods, dairy products, and blended food products.

10. The prepared food product of claim 9, wherein said baked prepared foods, dairy products, and blended food products are selected from the group consisting of pies, cookies, crackers, frozen desserts, creams, cheeses, spreads, salad dressing, margarines, and mayonnaise.

11. A method of aiding a person to increase the HDL concentration and the HDL/LDL concentration ratio in the serum of said person by providing a dietary fat composition having a balance between a sufficient and required proportion of cholesterol-free saturated fatty acids and a sufficient and required, but not excessive proportion of polyunsaturated fatty acids comprising linoleic acid in said dietary fat composition, while the remaining proportion of fatty acids and energy from said dietary fat composition is provided by monounsaturated fatty acids comprising oleic acid, wherein said saturated fatty acids constitute between 20% and 40% by weight of said dietary fat composition, and wherein said linoleic acid constitutes between 15% and 40% by weight of said dietary fat composition;

wherein said HDL concentration and said HDL/LDL concentration ratio will increase when the daily dietary fat accounts for between 15% and 45% of the total dietary energy and contains one part by weight polyunsaturated fat and at least one part by weight cholesterol-free saturated fat, wherein said daily dietary fat comprises linoleic acid and at least one saturated fatty acid selected from the group including lauric acid, myristic acid and palmitic acid, said linoleic acid constituting between 15% and 40% by weight of said daily dietary fat and said saturated fatty acid constituting between 20% and 40% by weight of said daily dietary fat.

12. A method of increasing the HDL concentration and the HDL/LDL concentration ratio in human serum by providing a balance between a sufficient and required proportion of cholesterol-free saturated fatty acids in the daily dietary fat of said human and a sufficient and required, but not excessive proportion of polyunsaturated fatty acids comprising linoleic acid in said dietary fat, while the remaining proportion of fatty acids and energy from said dietary fat is provided by monounsaturated fatty acids comprising oleic acid, said method comprising the step of: ingesting said dietary fat, wherein said saturated fatty acids are selected from the group consisting of palmitic acid, myristic acid, lauric acid, and combinations thereof, and constitute between 20% and 40% by weight of the daily dietary fat based upon said dietary fat accounting for 30% of the total dietary energy consumption, and wherein said linoleic acid constitutes between 15% and 40% by weight of said dietary fat, whereby the required proportional intake of said polyunsaturated fatty acids enhances the formation of HDL from VLDL and/or decreases the clearance of HDL, while an excessive proportional intake of said polyunsaturated fatty acids and said monounsaturated fatty acids is avoided to assure a sufficient dietary availability of said saturated fatty acids which are required for sufficient VLDL synthesis and HDL production, and wherein the food source for both said saturated and said polyunsaturated fatty acids comprises a genetically selected or engineered single vegetable oil species.

13. A method of increasing the HDL concentration and the HDL/LDL concentration ratio in human serum by providing a balance between a sufficient and required proportion of cholesterol-free saturated fatty acids in the daily dietary fat of said human and a sufficient and required, but not excessive proportion of polyunsaturated fatty acids comprising linoleic acid in said dietary fat, while the remaining proportion of fatty acids and energy from said dietary fat is provided by monounsaturated fatty acids comprising oleic acid, said method comprising the step of: ingesting said dietary fat, wherein said saturated fatty acids are selected from the group consisting of palmitic acid, myristic acid, lauric acid, and combinations thereof, and constitute between 20% and 40% by weight of the daily dietary fat based upon said dietary fat accounting for 30% of the total dietary energy consumption, and wherein said linoleic acid constitutes between 15% and 40% by weight of said dietary fat, whereby the required proportional intake of said polyunsaturated fatty acids enhances the formation of HDL from VLDL and/or decreases the clearance of HDL, while an excessive proportional intake of said polyunsaturated fatty acids and said monounsaturated fatty acids is avoided to assure a sufficient dietary availability of said saturated fatty acids which are required for sufficient VLDL synthesis and HDL production, and wherein the food source for both said saturated and said polyunsaturated fatty acids comprises a genetically selected or engineered single vegetable oil species.

14. A method of decreasing the LDL concentration in human serum comprising the step of providing saturated fatty acids selected from the group consisting of palmitic acid, myristic acid, lauric acid, and combinations thereof, in the daily diet in a proportion between 20% and 40% by weight of the daily dietary fat based upon said dietary fat accounting for 30% of the total dietary energy consumption, and maintaining a proportion of polyunsaturated fatty acids comprising linoleic acid in the daily diet at the expense of monounsaturated fatty acids comprising oleic acid and/or elaidic acid, wherein said linoleic acid constitutes between 15% and 40% by weight of said dietary fat, whereby removal of plasma VLDL remnants and LDL is maximized, and the production of LDL is reduced, and wherein the food source for both said saturated and said polyunsaturated fatty acids comprises a genetically selected or engineered single vegetable oil species.

15. A method of increasing the HDL and stabilizing or decreasing the LDL concentration in human serum comprising the step of providing saturated fatty acids selected from the group consisting of palmitic acid, myristic acid, lauric acid and combinations thereof, in the daily diet in a proportion between 20% and 40% by weight of the daily dietary fat based upon said dietary fat accounting for 30% of the total dietary energy consumption, whereby the production of VLDL, as the HDL precursor, is adequately sustained and is not rate limiting in HDL biosynthesis, and maintaining a proportion of polyunsaturated fatty acids comprising linoleic acid in the daily diet at the expense of monounsaturated fatty acids comprising oleic acid and/or elaidic acid, wherein said linoleic acid constitutes between 15% and 40% by weight of said dietary fat, whereby VLDL catabolism to HDL is facilitated and hepatic clearance of VLDL remnants and LDL is enhanced, and wherein the food source for both said saturated and said polyunsaturated fatty acids comprises a genetically selected or engineered single vegetable oil species.

16. A method of increasing the HDL concentration and the HDL/LDL concentration ratio in human serum comprising the step of consuming foods prepared using a cholesterol-free single fat or blended fat composition containing a ratio of one part by weight polyunsaturated fatty acids to at least one part by weight saturated fatty acids, wherein said single fat or blended fat composition comprises linoleic acid and at least one saturated fatty acid selected from the group including lauric acid, myristic acid, and palmitic acid, said linoleic acid constituting between 15% by weight and 40% by weight of said composition and said saturated fatty acid constituting between 20% and 40% by weight of said composition, whereby adequate dietary levels of saturated fatty acids in the absence of cholesterol stimulate VLDL synthesis and secretion by the liver, and adequate dietary levels of linoleic acid enhance LPL activity and generation of HDL from VLDL while stimulating the removal of VLDL remnants and LDL and concomitantly decreasing CETP activity and HDL catabolism, and wherein the food source for both said saturated and said polyunsaturated fatty acids comprises a genetically selected or engineered single vegetable oil species.

* * * * *

(12) EX PARTE REEXAMINATION CERTIFICATE (5653rd)
United States Patent
Sundram et al.

(10) Number: US 5,843,497 C1
(45) Certificate Issued: *Jan. 16, 2007

(54) INCREASING THE HDL LEVEL AND THE HDL/LDL RATIO IN HUMAN SERUM BY BALANCING SATURATED AND POLYUNSATURATED DIETARY FATTY ACIDS

(75) Inventors: Kalyana Sundram, Java (MY); Daniel Perlman, Arlington, MA (US); Kenneth C. Hayes, Wellesley, MA (US)

(73) Assignees: Brandeis University, Waltham, MA (US); Union Bank of California, Los Angeles, CA (US)

Reexamination Request:
No. 90/007,718, Sep. 14, 2005

Reexamination Certificate for:
Patent No.: 5,843,497
Issued: Dec. 1, 1998
Appl. No.: 08/626,461
Filed: Apr. 2, 1996

( * ) Notice: This patent is subject to a terminal disclaimer.

Related U.S. Application Data

(63) Continuation-in-part of application No. 08/418,641, filed on Apr. 7, 1995, now Pat. No. 5,578,334.

(51) Int. Cl.
*A23C 19/00* (2006.01)
*A23C 19/093* (2006.01)
*A23D 9/00* (2006.01)
*A23L 1/24* (2006.01)
*A23L 1/30* (2006.01)

(52) U.S. Cl. .......................... 426/2; 426/601; 426/607; 424/439

(58) Field of Classification Search ............... None
See application file for complete search history.

(56) References Cited

U.S. PATENT DOCUMENTS

| | | |
|---|---|---|
| 2,996,388 A | 8/1961 | Lindsay |
| 3,268,340 A | 8/1966 | Babayan et al. |
| 3,353,964 A | 11/1967 | Seiden |
| 3,634,100 A | 1/1972 | Merksem et al. |

OTHER PUBLICATIONS

K.G. Berger, The Use of Palm Oil Products in Margarines, PORIM technology, Aug. 1981, No. 5, Institiut Penyeldidkan Minyak, Kelapa Sawit Malaysia.

*Primary Examiner*—Evelyn Mei Huang

(57) ABSTRACT

A method of increasing the HDL concentration and the HDL/LDL concentration ratio in human serum by providing a balance between a sufficient and required proportion of cholesterol-free saturated fatty acids in the daily dietary fat of the human and a sufficient and required, but not excessive, proportion of polyunsaturated fatty acids comprising linoleic acid in dietary fat, while the remaining proportion of fatty acids and energy from the dietary fat is provided by monounsaturated fatty acids comprising oleic acid. The saturated fatty acids must constitute between 20% and 40% by weight of the daily dietary fat based upon dietary fat accounting for 30% of the total dietary energy consumption, and linoleic acid must constitute between 15% and 40% by weight of dietary fat. In this way, the required proportional intake of polyunsaturated fatty acids enhances the formation of HDL from VLDL and/or decreases the clearance of HDL, while an excessive proportional intake of polyunsaturated fatty acids and monounsaturated fatty acids is avoided to assure a sufficient dietary availability of saturated fatty acids which are required for sufficient VLDL synthesis and HDL production.

Figure 1:
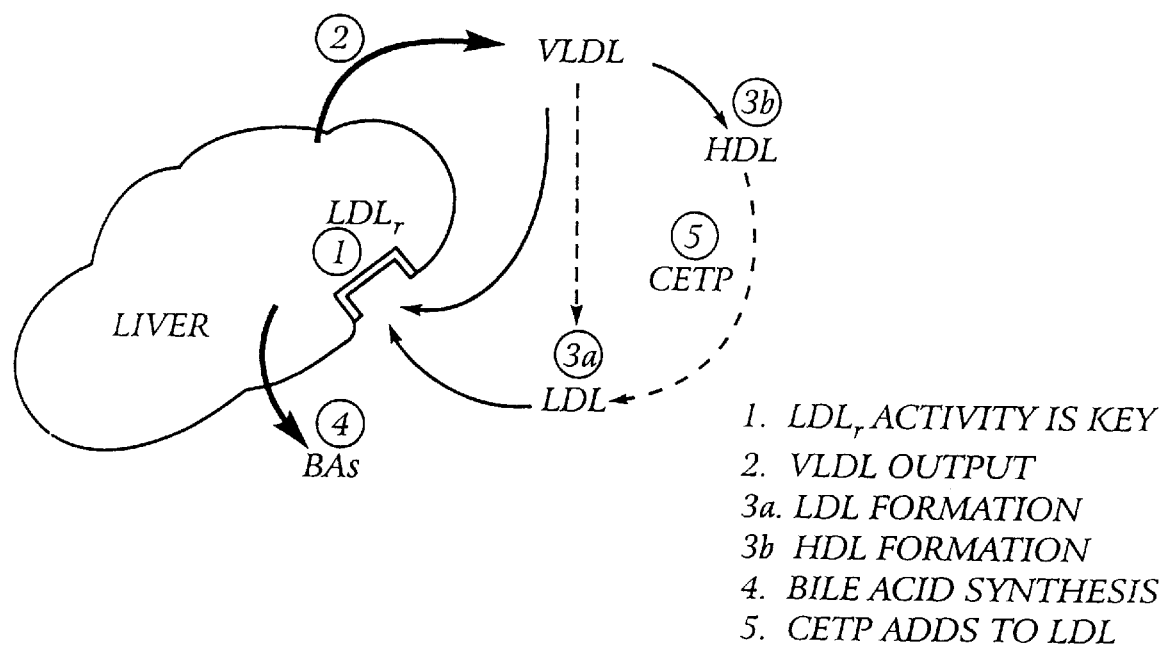

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–16 is confirmed.

New claims 17–42 are added and determined to be patentable.

17. *The fat composition of claim 1, comprising approximately 30% by weight palmitic acid and approximately 30% by weight linoleic acid plus linolenic acid.*

18. *The fat composition of claim 1, wherein said polyunsaturated fat comprises at least one polyunsaturated vegetable oil selected from the group consisting of corn oil, sunflower oil, safflower oil, soybean oil, cottonseed oil, canola oil, and peanut oil; and*

*said saturated fat comprises at least one saturated vegetable oil selected from the group consisting of palm fat, coconut fat and cocoa butter.*

19. *The fat composition of claim 18, wherein said palm fat is selected from the group consisting of palm oil, palm olein, and palm kernel oil.*

20. *The fat composition of claim 1, wherein said fat composition further comprises at least one polyunsaturated fatty acid selected from the group consisting of α-linolenic acid, eicosapentenoic acid (EPA), and docosahexenoic acid (DHA).*

21. *The fat composition of claim 1, wherein said fat composition consists of a mixture of two vegetable fats.*

22. *The fat composition of claim 1, wherein said fat composition comprises less than 5% by weight stearic acid.*

23. *The fat composition of claim 1, wherein greater than 50% by weight of said saturated fatty acids is palmitic acid.*

24. *The fat composition of claim 1, wherein the weight ratio of polyunsaturated fatty acids to saturated fatty acids is approximately 1:1.*

25. *The fat composition of claim 1, wherein the weight ratio of polyunsaturated fatty acids to saturated fatty acids is between 0.5:1.0 and 2.0:1.0.*

26. *The fat composition of claim 1, wherein said fat composition includes at least one saturated fat selected from the group consisting of palm oil, palm olein, palm kernel oil, coconut fat and coca butter; and at least one unsaturated fat selected from the group consisting of corn oil, sunflower oil, safflower oil, cottonseed oil, canola oil, and peanut oil.*

27. *The fat composition of claim 1, wherein said fat composition includes at least one saturated fat selected from the group consisting of palm olein, palm kernel oil, coconut fat and coca butter; and at least one unsaturated fat selected from the group consisting of corn oil, sunflower oil, safflower oil, cottonseed oil, canola oil, and peanut oil.*

28. *The fat composition of claim 1, wherein the weight ratio of polyunsaturated fats to saturated fats is not 1:1.*

29. *The prepared food product of claim 8, wherein said polyunsaturated fat comprises at least one polyunsaturated vegetable oil selected from the group consisting of corn oil, sunflower oil, safflower oil, soybean oil, cottonseed oil, canola oil, and peanut oil; and*

*said saturated fat comprises at least one saturated vegetable oil selected from the group consisting of palm fat, coconut fat and cocoa butter.*

30. *The prepared food product of claim 29, wherein said palm fat is selected from the group consisting of palm oil, palm olein, and palm kernel oil.*

31. *The prepared food product of claim 8, wherein said fat composition further comprises at least one polyunsaturated fatty acid selected from the group consisting of α-linolenic acid, eicosapentenoic acid (EPA), and docosahexenoic acid (DHA).*

32. *The prepared food product of claim 8, wherein said fat composition consists of a mixture of two vegetable fats.*

33. *The prepared food product of claim 8, wherein said fat composition comprises less than 5% by weight stearic acid.*

34. *The prepared food product of claim 8, wherein greater than 50% by weight of said saturated fatty acids is palmitic acid.*

35. *The prepared food product of claim 8, wherein the weight ratio of polyunsaturated fatty acids to saturated fatty acids is approximately 1:1.*

36. *The prepared food product of claim 8, wherein the weight ratio of polyunsaturated fatty acids to saturated fatty acids is between 0.5:1.0 and 2.0:1.0.*

37. *The prepared food product of claim 8, wherein said fat composition includes at least one saturated fat selected from the group consisting of palm oil, palm olein, palm kernel oil, coconut fat and coca butter; and at least one unsaturated fat selected from the group consisting of corn oil, sunflower oil, safflower oil, cottonseed oil, canola oil, and peanut oil.*

38. *The prepared food product of claim 8, wherein said fat composition includes at least one saturated fat selected from the group consisting of palm olein, palm kernel oil, coconut fat and coca butter; and at least one unsaturated fat selected from the group consisting of corn oil, sunflower oil, safflower oil, soybean oil, cottonseed oil, canola oil, and peanut oil.*

39. *The prepared food product of claim 8, wherein the weight ratio of polyunsaturated fats to saturated fats is not 1:1.*

40. *The fat composition of claim 1, further comprises between 20% and 50% by weight oleic acid.*

41. *The prepared food product of claim 8, wherein the fat composition further comprises between 20% and 50% by weight oleic acid.*

42. *The prepared food product of claim 8, wherein the fat composition comprises approximately 30% by weight palmitic acid and approximately 30% by weight linoleic acid plus linolenic acid.*

\* \* \* \* \*